US010064406B2

(12) United States Patent
Chan et al.

(10) Patent No.: US 10,064,406 B2
(45) Date of Patent: Sep. 4, 2018

(54) POLYMERIC SORBENT FOR REMOVAL OF IMPURITIES FROM WHOLE BLOOD AND BLOOD PRODUCTS

(75) Inventors: Phillip P. Chan, Cherry Hill, NJ (US); Vincent J. Capponi, Monmouth Junction, NJ (US); Thomas D. Golobish, Princeton, NJ (US); Humayra Begum Ali, Princeton, NJ (US)

(73) Assignee: CytoSorbents Corporation, Monmouth Junction, NJ (US)

( * ) Notice: Subject to any disclaimer, the term of this patent is extended or adjusted under 35 U.S.C. 154(b) by 0 days.

(21) Appl. No.: 13/344,166

(22) Filed: Jan. 5, 2012

(65) Prior Publication Data

US 2013/0011824 A1 Jan. 10, 2013

Related U.S. Application Data

(60) Provisional application No. 61/430,374, filed on Jan. 6, 2011.

(51) Int. Cl.
| | | |
|---|---|---|
| *A01N 1/02* | (2006.01) |
| *B01J 20/26* | (2006.01) |
| *B01J 20/28* | (2006.01) |
| *B01J 20/32* | (2006.01) |

(52) U.S. Cl.
CPC ......... *A01N 1/0263* (2013.01); *A01N 1/0278* (2013.01); *B01J 20/267* (2013.01); *B01J 20/28004* (2013.01); *B01J 20/28069* (2013.01); *B01J 20/28078* (2013.01); *B01J 20/327* (2013.01); *B01J 20/328* (2013.01); *B01J 20/3208* (2013.01); *B01J 20/3272* (2013.01); *Y10T 29/49826* (2015.01); *Y10T 428/2982* (2015.01)

(58) Field of Classification Search
None
See application file for complete search history.

(56) References Cited

U.S. PATENT DOCUMENTS

| | | | | |
|---|---|---|---|---|
| 4,064,042 A | * | 12/1977 | Kunin | 210/692 |
| 4,273,894 A | * | 6/1981 | Mucke et al. | 525/228 |
| 4,897,200 A | | 1/1990 | Smakman | |
| 4,952,322 A | * | 8/1990 | Sugiyama et al. | 210/679 |
| 5,211,850 A | * | 5/1993 | Shettigar | A61M 1/3472 |
| | | | | 210/195.2 |
| 6,048,464 A | | 4/2000 | Tanaka et al. | |
| 6,238,795 B1 | | 5/2001 | Strom et al. | |
| 2002/0197252 A1 | | 12/2002 | Brady et al. | |
| 2004/0185544 A9 | | 9/2004 | Hei | |
| 2005/0176678 A1 | | 8/2005 | Horres et al. | |
| 2008/0119576 A1 | | 5/2008 | Young et al. | |

FOREIGN PATENT DOCUMENTS

| | | |
|---|---|---|
| EP | 0512527 | 11/1992 |
| EP | 0799645 | 8/1997 |
| JP | 1189346 | 7/1989 |
| JP | 0558707 | 8/1993 |
| JP | 0588844 | 12/1993 |
| JP | 6126167 | 5/1994 |
| JP | 11290662 | 10/1999 |
| JP | 2007/252893 | 10/2007 |
| JP | 2008/069346 | 3/2008 |
| JP | 2009/125265 | 6/2009 |
| JP | 2009/165667 | 7/2009 |
| JP | 2010/057745 | 3/2010 |
| JP | 2010/201345 | 9/2010 |
| WO | WO 99/034914 | 7/1999 |
| WO | WO 00/043120 | 7/2000 |
| WO | WO 00/062836 | 10/2000 |
| WO | WO 02/053251 | 7/2002 |
| WO | WO 03/057356 | 7/2003 |
| WO | WO 2003/078023 | 9/2003 |
| WO | WO 2004/064988 | 8/2004 |
| WO | WO 2008/075951 | 6/2008 |
| WO | WO 2009/061759 | 5/2009 |
| WO | WO 2009/140897 | 11/2009 |
| WO | WO 2009/158027 | 12/2009 |
| WO | WO 2010/075061 | 7/2010 |
| WO | WO 2010/117668 | 10/2010 |

OTHER PUBLICATIONS

International Patent Application No. PCT/US2012/020429: International Search Report and Written Opinion of the International Searching Authority dated May 8, 2012, 14 pages.

* cited by examiner

*Primary Examiner* — Thomas J Visone (57) ABSTRACT

The invention concerns methods of treating blood, blood products or physiologic fluid to maximize shelf life and/or minimizing transfusion related complications such as non-hemolytic transfusion reactions such as fever, transfusion-related acute lung injury (TRALI), transfusion associated dyspnea (TAD), and allergic reactions by removing undesirable molecules in the blood, blood product or physiologic fluid milieu through use of a sorbent.

28 Claims, 9 Drawing Sheets

Figure 1. Plot of pore volume as a function of the pore diameter.

Figure 2. Modified Polystyrene 25mL pipette for slurry transfer

Figure 3. Modified Bag Spike
(Holes drilled in spike, strip of 200 micron screen inserted in the end)

Figure 4. Removal of Hemoglobin from Phosphate Buffered Saline

Figure 5. Removal of Hemoglobin from New Human Blood

Figure 6. Human IgG from Human Blood

Figure 7. LysoPC Adsorption from Human Blood

Figure 8. IL-7 Adsorption from Human Blood

Figure 9. IL-8 Adsorption from Human Blood

Figure 10. TNFα Adsorption from Human Blood

POLYMERIC SORBENT FOR REMOVAL OF IMPURITIES FROM WHOLE BLOOD AND BLOOD PRODUCTS

RELATED APPLICATIONS

This application claims benefit to U.S. Provisional Application Ser. Nos. 61/430,374, filed Jan. 6, 2011 the disclosure of which is incorporated herein by reference in its entirety.

TECHNICAL FIELD

The present invention concerns compositions and methods useful in the removal of cytokines, bioactive lipids, free hemoglobin, membrane or cellular degradation products, inflammatory mediators, vasoactive substances, foreign antigens, drugs, antibodies from blood and blood products, and other substances that can cause unwanted transfusion reactions.

BACKGROUND

The transfusion of whole blood or derivatives of whole blood ("blood products") are literally the lifeblood of patients with a range of conditions from severe trauma to surgery to cancer. According to the American Red Cross, there are more than 14 million packed red blood cell (pRBC) transfusions per year in the United States with 1 in every ten admissions to US hospitals requiring a blood transfusion on average. A similar number of transfusions of other fractions of whole blood, or blood products, such as platelets, white blood cells, plasma, albumin, immunoglobulins, clotting factors and cryoprecipitate, are administered each year. The critical need for blood extends to the military, where logistics of blood transport and storage are complicated and 8% of all hospital admissions during Operation Iraqi Freedom required massive transfusions, defined as more than 10 units of blood in the first 24 hours. Whole blood and blood products will be collectively referred to herein as "blood".

Blood has a limited life span. A typical pRBC unit has a usable life of only 42 days while platelets must be used within 5 days of donation. This, coupled with the high demand for blood, has led to periodic blood shortages. But many medical experts believe fresh blood should be used even sooner, within 2-4 weeks. Retrospective studies have implicated transfusions of "older" blood with an increased risk of non-hemolytic transfusion reactions such as fever, transfusion related acute lung injury (TRALI), transfusion associated dyspnea (TAD), allergic reactions, infection, death and other complications. In one of these studies, the risk of in-hospital death increased by 2% for each day a packed red cell unit aged. Because of this, extending the useful life of blood products and improving the quality of blood would be helpful.

SUMMARY

In some aspects, the invention concerns blood purification devices comprising: (a) a compliant container suitable for the storage of blood, blood product or physiologic fluid; (b) sorbent comprising hemocompatible material suitable for treating blood, blood product or physiologic fluid, the sorbent performing at least one of (i) increasing shelf life of the blood, blood product or physiologic fluid, (ii) maintaining freshness of new blood, blood product or physiologic fluid, and (iii) removing undesirable molecules from the blood, blood product or physiologic fluid; where the sorbent is contained within the compliant container.

In certain aspects, the invention concerns sorbent compositions, comprising a plurality of particles characterized as having a diameter in the range of from about 0.1 micron meters to about 2 centimeters, the particles comprising a hemocompatible porous polymer characterized as having a total pore volume of pore sizes in the range of from 10 Å to 10,000 Å, the total pore volume being in the range of from about 0.5 cc/g to about 3.0 cc/g based on dry polymer weight.

The invention also concerns methods of treating blood, blood product or physiologic fluid that (i) increase shelf life, (ii) maintain freshness of new blood, and/or (iii) remove undesirable molecules by use of a sorbent, the sorbent being contained within a compliant container suitable for the storage of blood, blood product or physiologic fluid and the sorbent being in a plurality of solid forms that are substantially free-flowing within the compliant container. In some embodiments the blood, blood product or physiologic fluid is a stored blood, blood product or physiologic fluid. In some embodiments, the blood, blood product or physiologic fluid is treated prior to storage.

Certain aspects of the invention concern methods of making a blood, blood product or physiologic fluid purification device comprising placing sorbent comprising hemocompatible material in a compliant container suitable for the storage of blood, blood products, or physiological fluid; wherein the hemocompatible material suitable for treating blood, blood product, or physiologic fluid, the sorbent performing at least one of (i) increasing shelf life of the blood, blood product or physiologic fluid, (ii) maintaining freshness of new blood, blood product or physiologic fluid, and (iii) removing undesirable molecules from the blood, blood product or physiologic fluid; and the sorbent being contained within said compliant container and said sorbent being in a plurality of solid forms that are substantially free-flowing within said compliant container.

The invention also concerns methods of treating blood, blood product, or physiologic fluid, said method comprising: (a) contacting the blood, blood product, or physiologic fluid with a sorbent, the sorbent performing at least one of (i) increasing shelf life, (ii) maintaining freshness of new blood, and/or (iii) removing undesirable molecules; and (b) placing the blood, blood product, or physiologic fluid from step (b) in a container for storage or into an animal. In some embodiments, the animal is a human. In some embodiments, the contacting takes place in a filter device. The filter may be used when administering blood to a patient between the blood bag (or potentially integrated into the blood bag) and the patient. The filter may also be used between a blood donor and the whole blood collection bag. In another embodiment, the filter may be used between the whole blood collection bag and the blood storage bag.

Hemocompatible material suitable for treating stored blood and blood products include polymeric material, pyrolyzed polymeric material, ceramic material, sol-gel material, metal, hybrid material, biological material, coated materials, Y-Carbon Products (Hemocompatible activated pyrolyzed carbon beads), CarboRx (activated carbon), hemosorbent, enterosorbent, NanoTune X (Biocompatible sorbent carbon material), Gambro (activated carbon filter device), Adsorba 150 & 300, Jafron Biomedical Co. (neutral porous polymer resin-pyrolyzed), HA330 Hemoperfusion Cartridge, HA130 (uremic toxins), the HA230 (drugs, lipophilic, hydrophobic or protein binding drugs), HA 280 (immunoadsorption), HA330 (cytokines, endotoxin for sepsis and SIRS), HA330-

II (toxins related to hepatic failure), Kaneka (modified cellulosic porous beads), Lixelle CTR, Ube Industries (Cellulosic bead crosslinked with hexamethylene-di-isocyanate) CF-X, ExThera Medical (Heparin coated polyurethane solid beads), Seraph, Toray industries, Inc. CYT-860 (polystyrene-based conjugated fiber reinforced with polypropylene) and silica based mesoporous materials.

In one embodiment of the invention, transfusion related complications such as non-hemolytic transfusion reactions such as fever, transfusion related acute lung injury (TRALI), transfusion associated dyspnea (TAD), allergic reactions are mitigated by removing undesirable molecules from blood through use of a sorbent. Use of the sorbent to remove undesirable products from transfusable blood can also extend the useful shelf life of this blood by, for example, removing undesirable products that accumulate during storage. These undesirable products found in blood are herein collectively referred to as Biologically Active Molecules (BAM)s. BAMs are defined as any substance or molecule that can, by itself or in combination with other BAMs, cause a biological, cellular or physiologic process. During blood transfusions, BAMs can elicit an undesirable physiologic response in the recipient of the transfused blood, such as TRALI, TAD, and others. For example, anti-human leukocyte antigen antibodies are BAMs linked to severe cases of TRALI. Prions, another example of a BAM, can cause Creutzfeldt-Jakob disease or subacute spongiform encephalopathy. A subset of BAMs are biological response modifiers (BRMs), that are substances that have an effect on the immune system. These include, for example, cytokines, chemokines, antibodies, glycoproteins, and growth factors. Cytokines found in transfusable blood can cause fever in the recipient.

In another embodiment, BAMs present in blood and blood products such as drugs, inflammatory mediators and stimulators such as cytokines, chemokines, interferons, nitric oxide, thromboxanes, leukotrienes, platelet,-activating factor, prostaglandins, glycoproteins, kinins, kininogens, complement factors, cell-adhesion molecules, superantigens, monokines, free radicals, proteases, arachidonic acid metabolites, prostacyclins, beta endorphins, myocardial depressant factors, anandimide, 2-arachadonylglycerol, tetrahydrobiopterin, histamine, bradykinin, soluble CD40 ligand, serotonin, hemoglobin, bioactive lipids, antibodies, antigens, prions, toxins, endotoxins, membrane or cellular components, and other BRMs are removed by the sorbent. These BAMs may have been present in the donor's blood at the time the blood donation was made or may develop over time as the blood is processed, or is in storage, or as part of the aging process.

In another embodiment the donated blood is treated with a sorbent to remove undesirable antibodies such as antileukocyte antibodies, and anti-human leukocyte antigen antibodies, at the time of donation, during storage, or at the point of use.

In another embodiment, polymers comprise particles having a diameter in the range for 0.1 micron meters to 2 centimeters. Certain polymers are in the form of powder, beads or other regular or irregularly shaped particulates. The pore structure of some polymers is such that the total pore volume of pore size in the range of 10 Å to 10,000 Å is greater than 0.5 cc/g to 3.0 cc/g dry polymer and a preferred embodiment of >50% pore volume between 10 Å to 6,000 Å. In some embodiments, the polymer has a pore structure such that the total pore volume of pore size in the range of 10 Å to 10,000 Å is greater than 0.5 cc/g to 3.0 cc/g dry polymer; wherein the ratio of pore volume between 10 Å to 10,000 Å (pore diameter) to pore volume between 500 Å to 3,000 Å (pore diameter) of the polymer is smaller than 7:1; and the ratio of pore volume between 10 Å to 10,000 Å (pore diameter) to pore volume between 10 Å to 6,000 Å (pore diameter) of the polymer is ≤2:1.

Certain polymers have a pore structure such that the total pore volume of pore size in the range of 20 Å to 10,000 Å is greater than 0.5 cc/g to 3.0 cc/g dry polymer and a preferred embodiment of >50% pore volume between 20 Å to 6,000 Å. In some embodiments, the polymer has a pore structure such that the total pore volume of pore size in the range of 20 Å to 10,000 Å is greater than 0.5 cc/g to 3.0 cc/g dry polymer; wherein the ratio of pore volume between 20 Å to 10,000 Å (pore diameter) to pore volume between 500 Å to 3,000 Å (pore diameter) of the polymer is smaller than 7:1; and the ratio of pore volume between 20 Å to 10,000 Å (pore diameter) to pore volume between 20 Å to 6,000 Å (pore diameter) of the polymer is ≤2:1.

In yet other embodiments, the pore structure of some polymers is such that the total pore volume of pore size in the range of 50 Å to 10,000 Å is greater than 0.5 cc/g to 3.0 cc/g dry polymer and a preferred embodiment of >50% pore volume between 50 Å to 6,000 Å. In some embodiments, the polymer has a pore structure such that the total pore volume of pore size in the range of 50 Å to 10,000 Å is greater than 0.5 cc/g to 3.0 cc/g dry polymer; wherein the ratio of pore volume between 50 Å to 10,000 Å (pore diameter) to pore volume between 500 Å to 3,000 Å (pore diameter) of the polymer is smaller than 7:1; and the ratio of pore volume between 50 Å to 10,000 Å (pore diameter) to pore volume between 50 Å to 6,000 Å (pore diameter) of the polymer is ≤2:1.

Some preferred polymers comprise residues from one or more monomers selected from divnylbenzene and ethylvinylbezene, styrene, ethylstyrene, acrylonitrile, butyl methacrylate, octyl methacrylate, butyl acrylate, octyl acrylate, cetyl methacrylate, cetyl acrylate, ethyl methacrylate, ethyl acrylate, vinyltoluene, vinylnaphthalene, vinylbenzyl alcohol, vinylformamide, methyl methacrylate, methyl acrylate, trivinylbenzene, divinylnaphthalene, trivinylcyclohexane, divinylsulfone, trimethylolpropane trimethacrylate, trimethylolpropane dimethacrylate, trimethylolpropane triacrylate, trimethylolpropane diacrylate, pentaerythritol dimethacrylate, pentaerythritol trimethacrylate, pentaerythritol tetramethacrylate, pentaerythritol diacrylate, pentaerythritol triiacrylate, pentaerythritol tetraacrylate, dipentaerythritol dimethacrylate, dipentaerythritol trimethacrylate, dipentaerythritol tetramethacrylate, dipentaerythritol diacrylate, dipentaerythritol triacrylate, dipentaerythritol tetraacrylate, divinylformamide and mixtures thereof.

Certain polymers useful in the invention are macroporous polymers prepared from the polymerizable monomers of styrene, divinylbenzene, ethylvinylbenzene, and the acrylate and methacrylate monomers such as those listed below by manufacturer. Rohm and Haas Company, (now part of Dow Chemical Company): (i) macroporous polymeric absorbents such as Amberlite™ XAD-1, Amberlite™ XAD-2, Amberlite™ XAD-4, Amberlite™ XAD-7, Amberlite™ XAD-7HP, Amberlite™ XAD-8, Amberlite™ XAD-16, Amberlite™ XAD-16 HP, Amberlite™ XAD-18, Amberlite™ XAD-200, Amberlite™ XAD-1180, Amberlite™ XAD-2000, Amberlite™ XAD-2005, Amberlite™ XAD-2010, Amberlite™ XAD-761, and Amberlite™ XE-305, and chromatographic grade adsorbents such as Amberchrom™ CG 71,s,m,c, Amberchrom™ CG 161,s,m,c, Amberchrom™ CG 300,s,m,c, and Amberchrom™ CG 1000,s,m,c. Dow Chemical Company: Dowex® Optipore™ L-493, Dowex®

Optipore™ V-493, Dowex® Optipore™ V-502, Dowex® Optipore™ L-285, Dowex® Optipore™ L-323, and Dowex® Optipore™ V-503. Lanxess (formerly Bayer and Sybron): Lewatit® VPOC 1064 MD PH, Lewatit® VPOC 1163, Lewatit® OC EP 63, Lewatit® S 6328A, Lewatit® OC 1066, and Lewatit® 60/150 MIBK. Mitsubishi Chemical Corporation: Diaion® HP 10, Diaion® HP 20, Diaion® HP 21, Diaion® HP 30, Diaion® HP 40, Diaion® HP 50, Diaion® SP70, Diaion® SP 205, Diaion® SP 206, Diaion® SP 207, Diaion® SP 700, Diaion® SP 800, Diaion® SP 825, Diaion® SP 850, Diaion® SP 875, Diaion® HP 1MG, Diaion® HP 2MG, Diaion® CHP 55A, Diaion® CHP 55Y, Diaion® CHP 20A, Diaion® CHP 20Y, Diaion® CHP 2MGY, Diaion® CHP 20P, Diaion® HP 20SS, Diaion® SP 20SS, and Diaion® SP 207SS. Purolite Company: Purosorb™ AP 250 and Purosorb™ AP 400.

In some embodiments, the polymer may be porous or non-porous. In certain preferred embodiments, the polymer is porous. In some embodiments, the polymer may be pyrolyzed. The pyrolyzation may be performed by methods known to those skilled in the art.

In some embodiments, the polymer is a coated polymer comprising at least one crosslinking agent and at least one dispersing agent. The dispersing agents can be selected from chemicals, compounds or materials such as hydroxyethyl cellulose, hydroxypopyl cellulose, poly(hydroxyethyl methacrylate), poly(hydroxyethyl acrylate), poly(hydroxypropyl methacrylate), poly(hydroxypropyl acrylate), poly(dimethylaminoethyl methacrylate), poly(dimethylaminoethyl acrylate), poly(diethylamimoethyl methacrylate), poly(diethylaminoethyl acrylate), poly(vinyl alcohol), poly(N-vinylpyrrolidinone), salts of poly(methacrylic acid), and salts of poly(acrylic acid) and mixtures thereof; the crosslinking agent selected from a group consisting of divinylbenzene, trivinylbenzene, divinylnaphthalene, trivinylcyclohexane, divinylsulfone, trimethylolpropane trimethacrylate, trimethylolpropane dimethacrylate, trimethylolpropane triacrylate, trimethylolpropane diacrylate, pentaerythrital dimethacrylates, pentaerythrital trimethacrylates, pentaerythrital, tetramethacrylates, pentaerythritol diacrylates, pentaerythritol triiacrylates, pentaerythritol tetraacrylates, dipentaerythritol dimethacrylates, dipentaerythritol trimethacrylates, dipentaerythritol tetramethacrylates, dipentaerythritol diacrylates, dipentaerythritol triacrylates, dipentaerythritol tetraacrylates, divinylformamide, heparin, polyethylene glycol, and mixtures thereof; and the polymer is developed simultaneously with the formation of the coating, wherein the dispersing agent is chemically bound to the surface of the polymer.

In yet another embodiment, the polymer is capable of sorbing protein molecules approximately 100 Daltons to about 1,000 Kilodaltons.

In some embodiments, the polymers may be derivatized. Some polymers may be modified with an antibody or ligand. Such polymer may be porous or solid.

For purposes of this invention, the term "total pore volume" is defined as the volume of all the pores in a polymer per unit mass and the term "effective pore volume" means any pore which selectively sorbs molecules. The term "capacity pore volume" is defined as the volume of the "capacity" of all the pores per unit mass of polymer and the term "effective pores" means the functional pores designed to sorb particular molecules. The term "capacity pore" is the total sum of the effective pores and transport pores. The term "transport pore" is defined as a pore that allows for a fast "transport" of the molecules to the effective pores and the term "transport pore volume" means the volume of the "transport" pores per unit mass of the polymer.

In some embodiments, the composition is contained in a suitable blood container with the blood or blood products. In certain embodiments, the invention concerns a blood storage bag comprising any of the compositions discussed herein. In some embodiments the composition is part of the storage container material that forms the container. In some embodiments, the composition is coated or deposited on the interior surface of the storage container and in direct contact with blood or blood products. In some embodiments the material is separated from the blood via membrane but fluid may pass through the membrane allowing BRMs to communicate with the composition but excluding cells such as white blood cells, red blood cells and platelets. Some methods further comprise separating the composition from the blood via filtration. In certain embodiments the filtration occurs while the blood is removed from the storage bag during transfusion to a patient. In some embodiments the sorbent in the blood container is in direct contact with the blood. In some embodiments the container contains a mixture of different bead types.

Certain embodiments concern filters comprising any of the composition discussed herein. Some embodiments, concern a filter cartridge comprising any of the composition discussed herein. Some devices of the invention are blood filtration devices comprising a filter or filter cartridge comprising the any of the composition discussed herein.

In some embodiments the composition is contained in a filter and either the blood from the donor at the time of donation is passed through the filter before placement into a suitable blood container or the blood or blood products in the blood container pass through the filter during transfusion into the patient. For purposes of this invention, the term "sorb" is defined as "taking up and binding by absorption and adsorption".

DETAILED DESCRIPTION OF ILLUSTRATIVE EMBODIMENTS

As required, detailed embodiments of the present invention are disclosed herein; it is to be understood that the disclosed embodiments are merely exemplary of the invention that may be embodied in various forms. Therefore, specific structural and functional details disclosed herein are not to be interpreted as limits, but merely as a basis for teaching one skilled in the art to employ the present invention. The specific examples below will enable the invention to be better understood. However, they are given merely by way of guidance and do not imply any limitation.

Three porous polymeric sorbents are characterized for their pore structures and their syntheses are described in Example 1, 2, and 3. The pore structure characterization is given in Example 3.

The synthesis process consists of (1) preparing the aqueous phase, (2) preparing the organic phase, (3) carrying out the suspension polymerization, and (4) purifying the resulting porous polymeric sorbent product (work-up).

Remaining examples demonstrate removal of unwanted substances from blood.

Example 1

Sorbent 1-11 Synthesis

Reactor Setup, Kettle (0.5 L) is fitted with over head stirrer, Multi-level stirrer blade, water cooled condenser, thermocouple, and bubbler. A gasket was installed between the top lid and bottom kettle. All unused ports are capped with the appropriate plug. Temperature is controlled with a heating mantle regulated by a temperature controller fitted with the above thermocouple.

Polymerization, The Polyvinyl Alcohol is dispersed in the water charge at room temperature (RT) and then heated to 70° C. The remaining salts (See Table 1, MSP, DSP, TSP, & Sodium Nitrite) are then dissolved in the water charge. The PVA and Salts solutions are heated to 80° C. with stirring.

The pre-mixed organic phase listed in Table 2 including the initiator is poured into the reactor onto the aqueous phase with the stirring speed set at the rpm for formation of the appropriate droplet size. Once temperature reaches the specified value start reaction timer (16 hours).

TABLE 1

Aqueous Phase Charges

| Item | Charge, g |
| --- | --- |
| Ultrapure Water | 231.26 |
| Polyvinyl Alcohol (PVA) | 0.68 |
| Monosodium Phosphate (MSP) | 0.71 |
| Disodium Phosphate (DSP) | 2.36 |
| Trisodium Phosphate (TSP) | 1.47 |
| Sodium Nitrite | 0.01 |
| Total | 236.48 |

Work-up, Mark solvent level. After cooling the solvent is siphoned out to bead level. Reactor is filled to mark with (RT) water and heated to 50° C. to 70° C. and stirred for 30 minutes, allowed to settle for 3 to 5 minutes and then siphoned out to bead level. Beads are washed 5 times in this manner. For polymers using cyclohexanol as a porogen 3 additional methanol in pot washes are added. Polymer 1 uses 3 in pot IPA washes. If indicated, the polymer is extracted via a Soxhlet apparatus with per Table 2 overnight. The polymer is steam stripped 6 hours and then dried in an oven overnight (~100° C.). This process results in a clean, dry porous sorbent in the form of spherical, porous polymer beads, Sorbent Polymers 1 to 11.

TABLE 2

| | Organic Charges, g | | | | | |
| --- | --- | --- | --- | --- | --- | --- |
| Sorbent/ Polymer # | Divinyl benzene (63%) | Divinyl benzene (80%) | Toluene | Isooctane | Cyclohexanol | Polyproplene glycol, PPG, Mw 3500 |
| 1 | 84.70 | | 55.78 | 64.07 | | |
| 2 | 83.03 | | | | 151.00 | |
| 3 | | 71.3 | | | 163.15 | |
| 4 | 129.55 | | | | 77.11 | 25.70 |
| 5 | 106.38 | | | | 107.80 | 19.02 |
| 6 | 106.38 | | | | 114.14 | 12.68 |
| 7 | 106.38 | | | | 115.73 | 11.10 |
| 8 | 94.73 | | | | 130.21 | 8.68 |
| 9 | 106.38 | | | | 109.07 | 17.76 |
| 10 | 124.05 | | 88.6 | | | |
| 11 | 129.55 | | | | 102.82 | |

| | Organic Charges, g | | | Reaction Conditions | Work-up, Conditions | |
| --- | --- | --- | --- | --- | --- | --- |
| Sorbent/ Polymer # | Polystyrene, Mw 230,000 | Benzoyl Peroxide (BPO) (97%) | Total, w/o BPO | Rxn Temp.° C. | 1st Soxhlet Solvent | 2nd Soxhlet Solvent |
| 1 | | 0.64 | 236.48 | 80 | | |
| 2 | | 0.84 | 234.03 | 87 | Methanol | |
| 3 | | 0.73 | 234.45 | 80 | Methanol | |
| 4 | | 1.32 | 232.37 | 80 | Acetone | |
| 5 | | 1.08 | 232.20 | 80 | Acetone | |
| 6 | | 1.08 | 233.20 | 80 | Acetone | |
| 7 | | 1.08 | 233.20 | 80 | Acetone | |
| 8 | | 0.96 | 233.62 | 80 | Acetone | |
| 9 | | 1.08 | 233.20 | 80 | Acetone | |
| 10 | 9.8 | 0.94 | 222.49 | 80 | Toluene | Acetone |
| 11 | | 1.32 | 232.37 | 80 | Methanol | |

Example 2

Pore Structure Characterization

Figure 1:
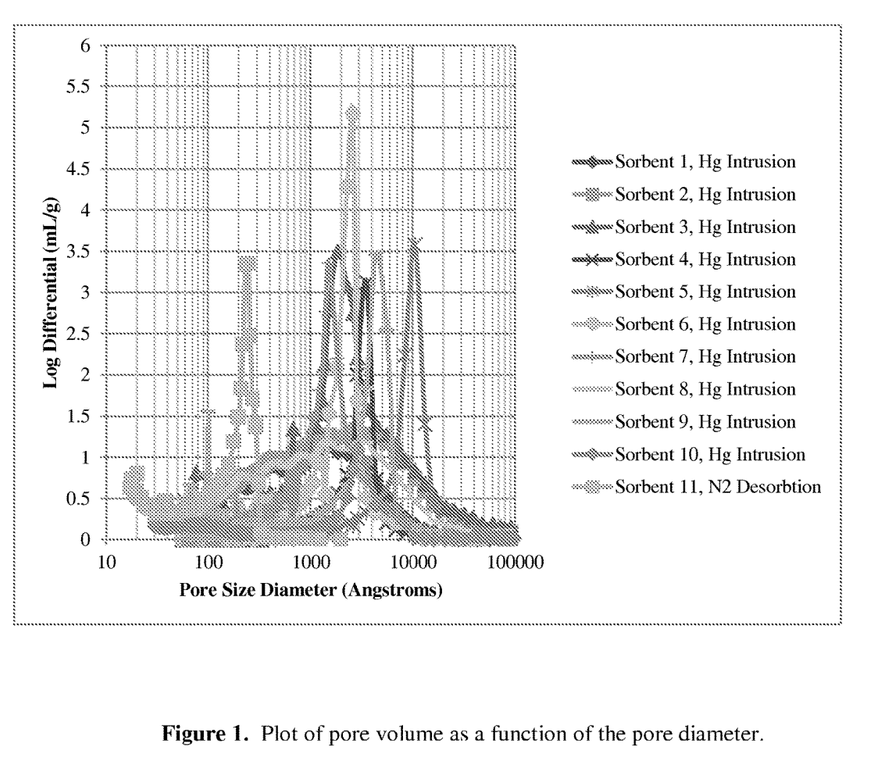
FIG. 1 presents a plot of pore volume as a function of the pore diameter.

The pore structures of the sorbent polymers were analyzed with a either Micromeritics AutoPore IV 9500 V1.09 a Mercury Penetrometer (Hg Intrusion instrument). The results are provided in FIG. 1 where the pore volume is plotted as a function of the pore diameter.

Example 3

Pore Structure Comparison to Biomolecule Adsorbtion

The pore structures of the sorbent polymers were compared to Cytochrome C, Human Serum Albumin, and Immunoglobulin G (IgG). Cytochrome C, ~12 kDa, was used as a surrogate for middle molecular weight proteins such as cytokines, Human Serum Albumin (67 kDa) as a surrogate for Hemoglobin (64 kDa) and IgG representing antibodies. The comparisons are shown in Table 3.

TABLE 3

| Sorbent/Polymer# | Pore Diameter Based off Log Differential Plot maximum (Å) | Pore Volume between 50-10000 Å (cc/g) | Pore Volume between 500-3000 Å (cc/g) | Percent of total Pore Volume between 500-3000 Å | Pore Volume Between 50-6000 Å (cc/g) | Percent of total Pore Volume between 50-6000 Å |
|---|---|---|---|---|---|---|
| 1 | 1395 | 1.72 | 0.93 | 54 | 1.68 | 98 |
| 2 | 2,594 | 2.31 | 1.17 | 51 | 2.11 | 91 |
| 3 | 1,830 | 2.47 | 1.71 | 69 | 2.29 | 93 |
| 4 | 3,498 | 0.94 | 0.74 | 79 | 0.93 | 99 |
| 5 | 10,483 | 1.01 | 0.13 | 13 | 0.42 | 42 |
| 6 | 2,591 | 1.46 | 1.24 | 85 | 1.44 | 98 |
| 7 | 1,510 | 1.63 | 1.28 | 79 | 1.59 | 97 |
| 8 | 2,839 | 1.84 | 1.46 | 79 | 1.77 | 96 |
| 9 | 4,337 | 1.32 | 0.52 | 39 | 1.29 | 97 |

| Sorbent/Polymer# | Ratio of pore volume between 50-10000 Å to pore volume between 500-3000 Å | Ratio of pore volume between 50-10000 Å to pore volume between 50-6000 Å | 3 hour Cytochrome C Removal (mg/g) | 3 hour Human Serum Albumin Removal (mg/g) | 3 hour Immunoglobulin G Removal (mg/g) |
|---|---|---|---|---|---|
| 1 | 1.85 | 1.02 | 53 | 313.5 | 152.1 |
| 2 | 1.97 | 1.09 | 109.5 | 204.8 | 385.5 |
| 3 | 1.44 | 1.08 | 91.7 | 176.1 | 289.2 |
| 4 | 1.27 | 1.01 | 9.7 | 107 | 103.9 |
| 5 | 7.77 | 2.39 | 0.4 | 101.3 | 38.8 |
| 6 | 1.18 | 1.02 | 34.4 | 77.4 | 128.1 |
| 7 | 1.27 | 1.03 | 62.4 | 228.3 | 266.8 |
| 8 | 1.26 | 1.04 | 49.4 | 102.8 | 140 |
| 9 | 2.54 | 1.03 | 11.4 | 90.6 | 89.3 |

Example 4

Adsorbtion Experiments

Setup and Initial Sampling
Blood and Polymer Preparation

Each polymer tested was initially prepared as a 50% slurry in 0.9% Saline. Blood was prepared by pooling 8 bags of non-Leukoreduced packed red blood cells ~400 mL (human, <4 days old type AB+) each to an empty 3 L saline bag (PVC, NDC 0409-7983-03) and gently mixed by gently rocking 10 times. The pooled blood was aliquot to 8 empty×500 mL saline bags, Part Number ND0409-7972-08, weighed and recorded for future reference. The test utilized 3 polymer and a no bead control:
Sorbent 1 (Polymer 1)
Sorbent 2 (Polymer 2)
Sorbent 3 (Polymer 3)
Control (No beads)

Figure 2:
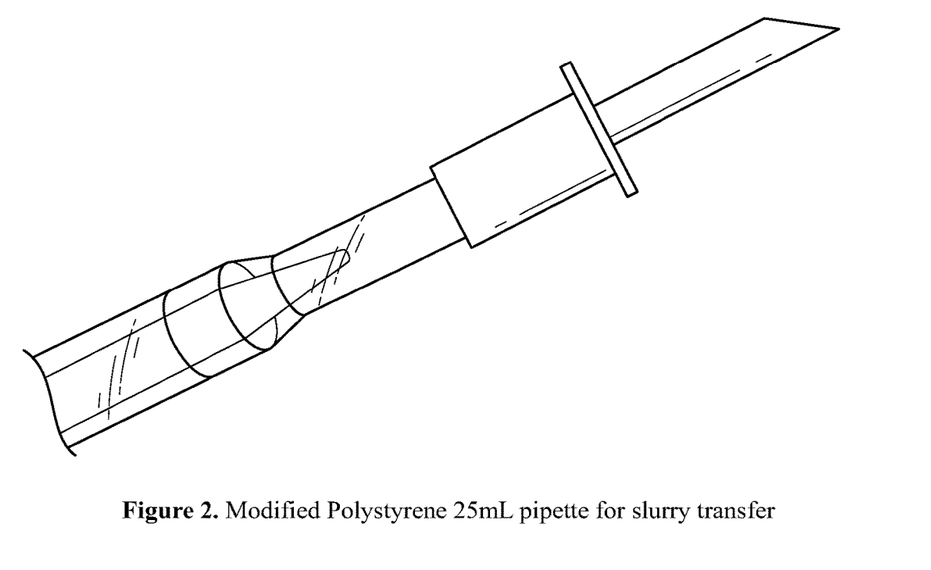
FIG. 2 presents a polymer transfer adaptor for blood experiments
Figure 3:
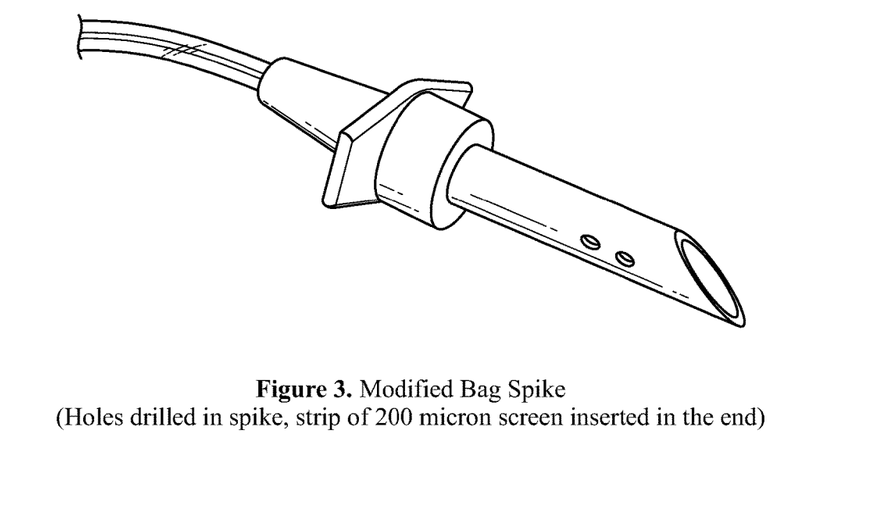
FIG. 3 presents a blood transfer adaptor for sample collection

Blood/Polymer Charge 80 mL of polymer slurry (50%) was charged to the empty 500 mL saline bags with a Modified Polystyrene 25 mL pipette FIG. 2 and the weight recorded. The pooled packed red blood cells were then transferred into emptied 500 mL saline bags that had been charged with the bead slurry (beads 10% of RBC volume) to be studied or no beads for the control and bag weights were recorded. Each bag was gently rocked back and forth 10 times to mix thoroughly. All blood stored at 5° C. for the duration of the experiment.

Sampling Day 1

On Day One Hematocrit for each sample bag was taken to account for dilution due to polymer slurry charged into each sample bag. Approximately 5 mls of blood were sampled into a red top vacutainer (BD 366430) for Cytokine/IgG analysis and a second polystyrene tube (BD 352099) was sampled using 5 mls of blood for Lysophosphatidylcholine analysis (LPC). Both the red top and polystyrene collection tubes were spun for 20 minutes and the supernatant separated into polypropylene and polystyrene cryo tubes, respectively and frozen at −25° C.

Sample Collection, Days 7, 14, 21, & 41

Sample bags were removed from the refrigerator and gently mixed by inverting 10 times and sampled for hematocrit. Sampling for Cytokine/IgG and LPC was performed identical to Day 1 sampling. All samples collected were stored at −25° C. until analyzed.

Hemoglobin Absorption from Phosphate Buffered Saline

Solution of Hemoglobin in Phosphate Buffered Saline was prepared at a concentration of approximately 11.00 mg/mL. Individual 50 mL polypropylene centrifuge tubes were used for each time point sampled, excluding the t=0 time point (the t=0 samples were taken directly from the Hemoglobin stock solution). 2.5 g of wet polymer with the interstitial saline removed and 22.5 mL of Hemoglobin solution were added to each centrifuge tube. The tubes were then placed on a platform rocker in a 4-8° C. refrigerator. At the appropriate time points, the applicable centrifuge tubes were removed from the refrigerator. Four samples were removed from each centrifuge tube, labeled, and frozen at −20° C. until analysis was performed.

Hemoglobin Absorption from "New" Human Blood—14 Day Aging Study

Three bags of freshly drawn blood were purchased. Upon receipt, the contents of the bags were pooled and approximately 350-400 mL of blood was distributed into two separate blood bags. 30 mL of 0.9% saline containing polymer beads (50% solids) was added to one of the bags (experiment), and 30 mL of 0.9% saline was added to the other (control). One blood sample was taken from the control bag, the result being used as the t=0 (initial) sample value. At each time point, one hematocrit sample and one blood sample was taken. The hematocrit value was measured and recorded, the blood sample was appropriately centrifuged and plasma samples were removed and stored in polypropylene sample vials at −20° C. until analysis was performed. The blood bags were placed on a platform rocker in a 4-8° C. refrigerator. At the appropriate time points, the blood bags were removed from the refrigerator and sampled as previously described. Once sampled, the bags were returned to the refrigerator.

Analysis of Samples from the Hemoglobin in Phosphate Buffered Saline, Hemoglobin in "New" Human Blood (14 Day Aging Study), and Real Time Aging (41-day) Study of Human Blood (IgG & LPC)

Figure 4:
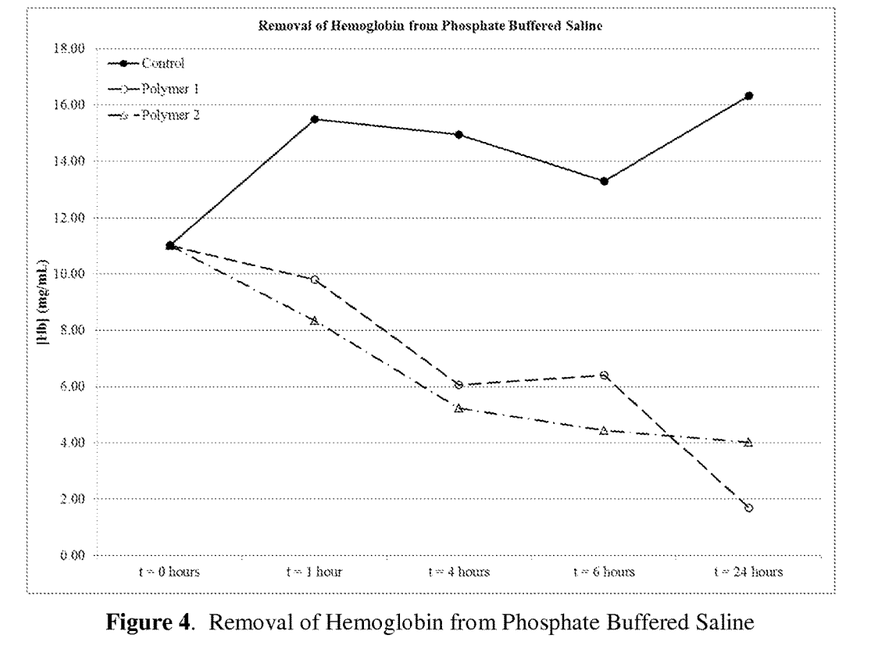
FIG. 4, presents a plot of adsorption of Hemoglobin from Phosphate Buffered Saline versus time
Figure 5:
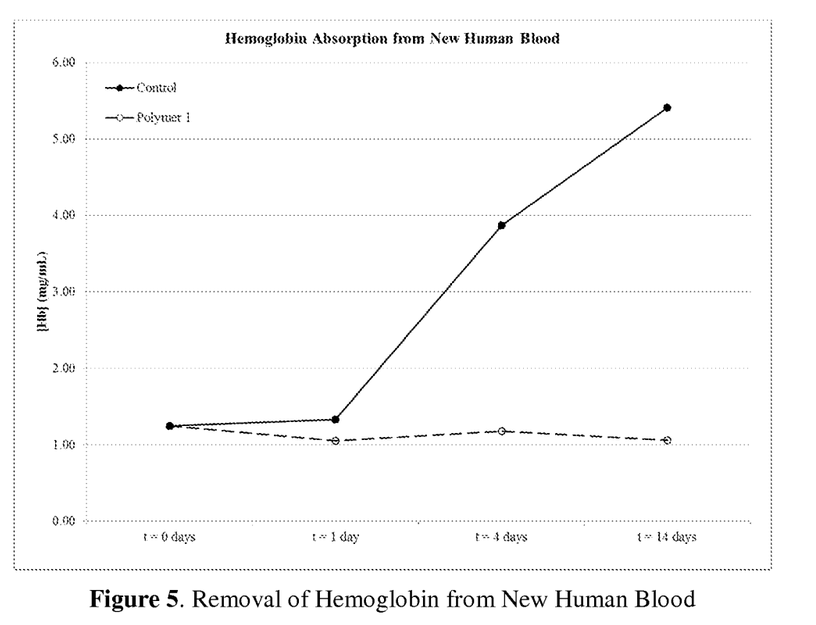
FIG. 5, presents a plot of adsorption of Hemoglobin from New Human Blood versus time

Human Hemoglobin Analysis; Analysis of Human Hemoglobin was conducted on the collected blood samples using Bethyl Laboratories Incorporated's Human Hemoglobin ELISA Kit, Catalog #E88-135. Analysis procedures were conducted according to the manual provided with the kit. See Table 4 & 5 for the resultant data and FIGS. 4 & 5 for a graphical representation.

This experiment represented a hemoglobin adsorption experiment under controlled conditions with known starting concentrations of hemoglobin.

TABLE 4

Hemoglobin Data (Phosphate Buffered Saline)

| Polymer ID | Sample Description | [Hb] (mg/mL) |
|---|---|---|
| Polymer 1 | t = 0 hours | 11.00 |
| | t = 1 hour | 9.79 |
| | t = 4 hours | 6.06 |
| | t = 6 hours | 6.41 |
| | t = 24 hours | 1.68 |
| Polymer 2 | t = 0 hours | 11.00 |
| | t = 1 hour | 8.35 |
| | t = 4 hours | 5.24 |
| | t = 6 hours | 4.46 |
| | t = 24 hours | 4.03 |
| Control | t = 0 hours | 11.00 |
| | t = 1 hour | 15.50 |
| | t = 4 hours | 14.96 |
| | t = 6 hours | 13.30 |
| | t = 24 hours | 16.33 |

This test was designed to show the dynamic removal of hemoglobin by the test polymers in a model system where hemoglobin is constantly generated by gently rocking the blood in a bag causing red blood cell lysis and release of hemoglobin.

TABLE 5

Hemoglobin Data ("New" Human Blood - 14 day Aging Study)

| Polymer ID | Sample Description | [Hb] (mg/mL) Corrected for Hematocrit |
|---|---|---|
| Polymer 1 | t = 0 days | 1.25 |
| | t = 1 day | 1.05 |
| | t = 4 days | 1.18 |
| | t = 14 days | 1.06 |
| Control | t = 0 days | 1.25 |
| | t = 1 day | 1.33 |
| | t = 4 days | 3.87 |
| | t = 14 days | 5.41 |

Figure 6:
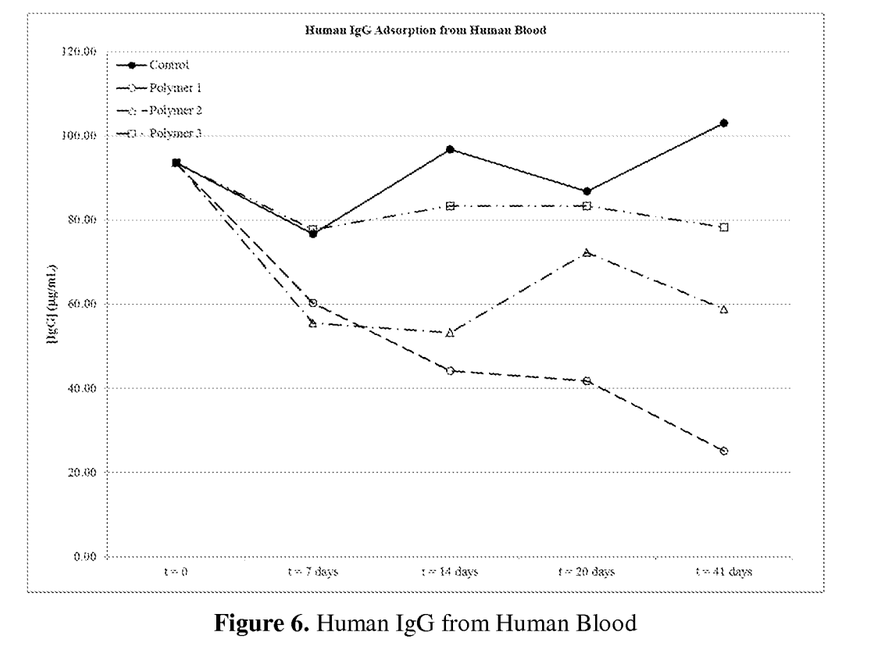
FIG. 6 presents a plot of adsorption of human IgG from human blood versus time.

Human Immunoglobulin G Analysis; Analysis of Human Immunoglobulin G was conducted on the collected blood samples using ZeptoMetrix Corporation's Immunotek Quantitative Human IgG ELISA Kit, Catalog #0801182. Analysis procedures were conducted according to the manual provided with the kit. See Table 6 for the resultant data and FIG. 6 for a graphical representation.

TABLE 6

| Polymer ID | Sample Description | [IgG] (μg/mL) Corrected for Hematocrit |
|---|---|---|
| Polymer 1 | t = 0 | 93.54 |
| | t = 7 days | 60.30 |
| | t = 14 days | 44.12 |
| | t = 20 days | 41.81 |
| | t = 41 days | 25.06 |
| Polymer 2 | t = 0 | 93.54 |
| | t = 7 days | 55.44 |
| | t = 14 days | 53.25 |
| | t = 20 days | 72.27 |
| | t = 41 days | 58.79 |
| Polymer 3 | t = 0 | 93.54 |
| | t = 7 days | 77.75 |
| | t = 14 days | 83.39 |
| | t = 20 days | 83.39 |
| | t = 41 days | 78.30 |
| Control | t = 0 | 93.54 |
| | t = 7 days | 76.68 |
| | t = 14 days | 96.82 |
| | t = 20 days | 86.86 |
| | t = 41 days | 103.10 |

Figure 7:
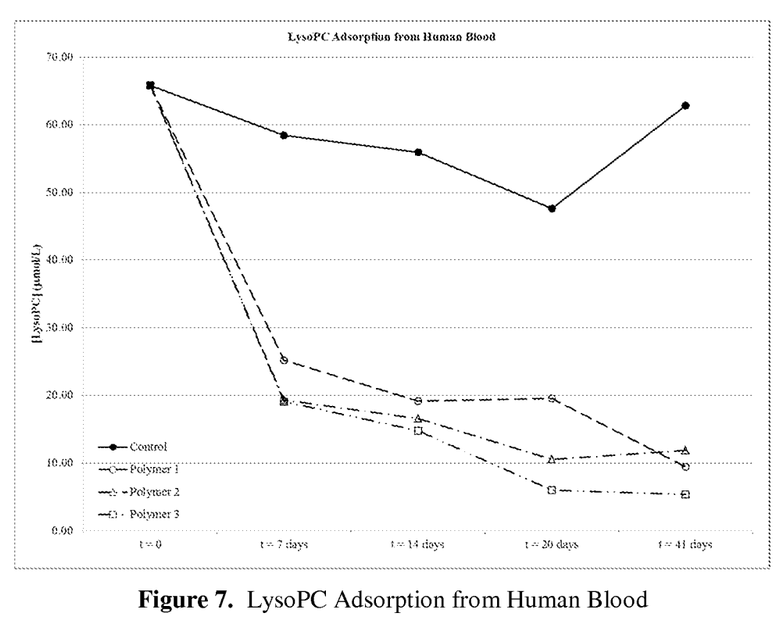
FIG. 7 presents a plot of LysoPC adsorption from human blood versus time.

Human Lysophosphatidylcholine Analysis; Analysis of Human Lysophosphatidylcholine was conducted on the collected blood samples using Cosmo Bio Company's AZWELL LPC Assay Kit, Catalog #ALF-274729843. Analysis procedures were conducted according to the manual provided with the kit (translated into English), with one exception: 700 nm filters are not currently available for the microplate reader in our facility (BioTek EL800). Therefore, we were unable to measure absorbance at this wavelength for avoidance of interference as recommended by the kit manufacturer. See Table 7 for the resultant data and FIG. 7 for a graphical representation.

TABLE 7

| Polymer ID | Sample Description | [LysoPC] (μmol/L) Corrected for Hematocrit |
|---|---|---|
| Polymer 1 | t = 0 | 65.85 |
|  | t = 7 days | 25.23 |
|  | t = 14 days | 19.18 |
|  | t = 20 days | 19.53 |
|  | t = 41 days | 9.40 |
| Polymer 2 | t = 0 | 65.85 |
|  | t = 7 days | 19.28 |
|  | t = 14 days | 16.57 |
|  | t = 20 days | 10.52 |
|  | t = 41 days | 11.84 |
| Polymer 3 | t = 0 | 65.85 |
|  | t = 7 days | 19.11 |
|  | t = 14 days | 14.73 |
|  | t = 20 days | 6.02 |
|  | t = 41 days | 5.33 |
| Control | t = 0 | 65.85 |
|  | t = 7 days | 58.41 |
|  | t = 14 days | 55.97 |
|  | t = 20 days | 47.63 |
|  | t = 41 days | 62.87 |

Figure 8:
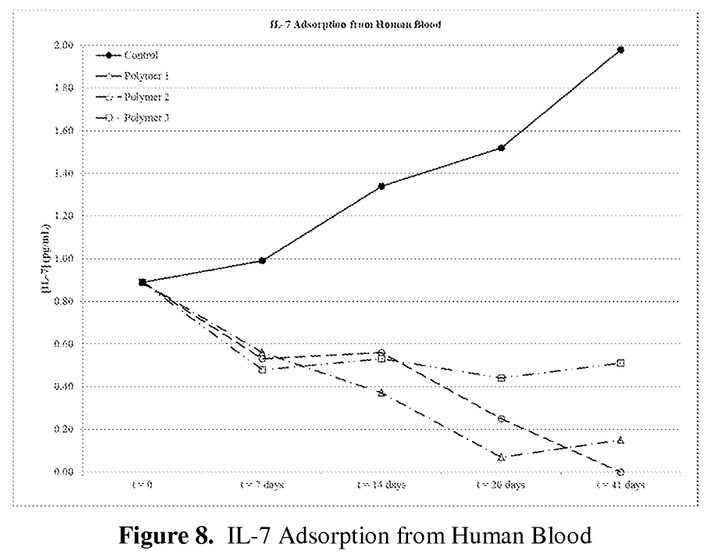
FIG. 8 presents a plot of IL-7 adsorption from human blood versus time.
Figure 9:
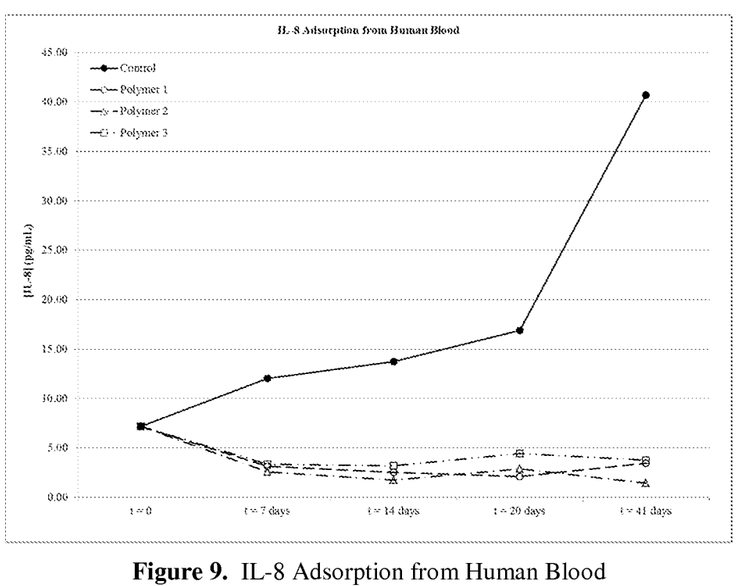
FIG. 9 presents a plot of IL-8 adsorption from human blood versus time.
Figure 10:
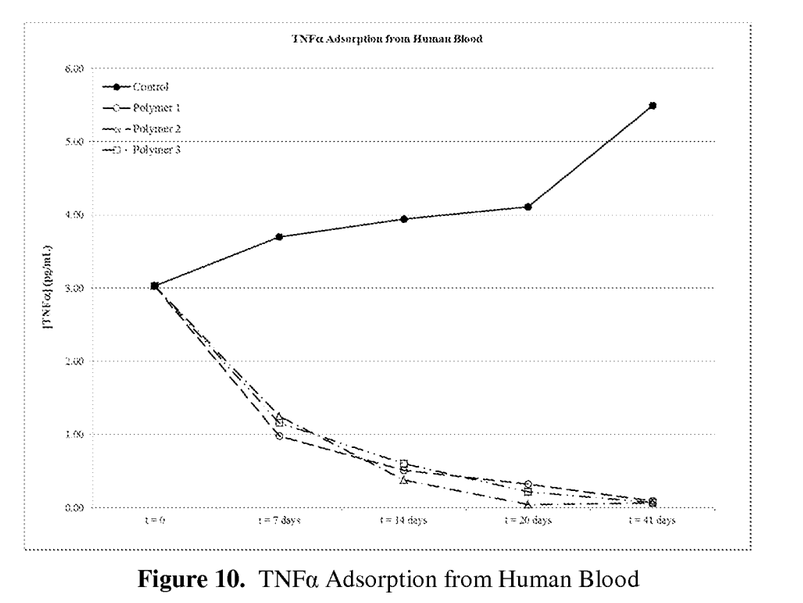
FIG. 10 presents a plot of TNFα adsorption from human blood versus time.

Human Cytokine Analysis; Analysis of thirteen Human Cytokines (IL-1β, IL-2, IL-4, IL-5, IL-6, IL-7, IL-8, IL-10, IL-12(p70), IL-13, IFNγ, GM-CSF, and TNFα) was conducted on the collected blood samples using Millipore's Milliplex MAP High Sensitivity Human Cytokine Magnetic Bead Kit, Catalog #HSCYTMAG-60SK. Analysis procedures were conducted according to the manual provided with the kit. Several analytes returned values below the lower limit of quantitation for the assay, and thus are not reported. See Table 8 for the resultant data and FIGS. 8, 9, & 10 for a graphical representation of each reported cytokine.

TABLE 8

| Polymer ID | Sample Description | [IL-7] (pg/mL) Corrected for Hematocrit | [IL-8] (pg/mL) Corrected for Hematocrit | [TNFα] (pg/mL) Corrected for Hematocrit |
|---|---|---|---|---|
| Polymer 1 | t = 0 | 0.89 | 7.17 | 3.03 |
|  | t = 7 days | 0.53 | 3.14 | 0.98 |
|  | t = 14 days | 0.56 | 2.54 | 0.51 |
|  | t = 20 days | 0.25 | 2.11 | 0.32 |
|  | t = 41 days | 0.00 | 3.44 | 0.09 |
| Polymer 2 | t = 0 | 0.89 | 7.17 | 3.03 |
|  | t = 7 days | 0.56 | 2.59 | 1.25 |
|  | t = 14 days | 0.37 | 1.74 | 0.38 |
|  | t = 20 days | 0.07 | 2.92 | 0.04 |
|  | t = 41 days | 0.15 | 1.46 | 0.06 |
| Polymer 3 | t = 0 | 0.89 | 7.17 | 3.03 |
|  | t = 7 days | 0.48 | 3.37 | 1.16 |
|  | t = 14 days | 0.53 | 3.21 | 0.60 |
|  | t = 20 days | 0.44 | 4.44 | 0.22 |
|  | t = 41 days | 0.51 | 3.79 | 0.07 |
| Control | t = 0 | 0.89 | 7.17 | 3.03 |
|  | t = 7 days | 0.99 | 12.04 | 3.70 |
|  | t = 14 days | 1.34 | 13.76 | 3.94 |
|  | t = 20 days | 1.52 | 16.89 | 4.11 |
|  | t = 41 days | 1.98 | 40.70 | 5.49 |

What is claimed:

1. A storage container for storage and purification of blood, blood product or physiologic fluid prior to transfusion into a patient, the storage container comprising:
    (a) said storage container being a compliant container suitable for the storage of blood, blood products or physiologic fluids;
    (b) sorbent comprising hemocompatible material suitable for treating blood, blood product or physiologic fluid, said sorbent performing at least one of (i) increasing shelf life of the blood, blood product or physiologic fluid, (ii) maintaining freshness of new blood, blood product or physiologic fluid, and (iii) removing undesirable molecules from the blood, blood product or physiologic fluid;
    said sorbent comprises cross-linked polymeric material derived from the reaction of a cross-linker with one or more of the following polymerizable monomers: divinylbenzene, styrene, ethylstyrene, acrylonitrile, butyl methacrylate, octyl methacrylate, butyl acrylate, octyl acrylate, cetyl methacrylate, cetyl acrylate, ethyl methacrylate, ethyl acrylate, vinyltoluene, vinylnaphthalene, vinylbenzyl alcohol, vinylformamide, methyl methacrylate, and methyl acrylate;
    wherein said sorbent comprises a hemocompatible surface comprising hydroxyethyl cellulose, hydroxypopyl cellulose, poly(hydroxyethyl methacrylate), poly(hydroxyethyl acrylate), poly(hydroxypropyl methacrylate), poly(hydroxypropyl acrylate), poly(dimethylaminoethyl methacrylate), poly(dimethylaminoethyl acrylate), poly(diethylamimoethyl methacrylate), poly(diethylaminoethyl acrylate), poly(vinyl alcohol), heparin, polyethylene glycol, poly(N-vinylpyrrolidinone), salts of poly(methacrylic acid), salts of poly (acrylic acid) or copolymers of mixtures thereof, wherein said hemocompatible surface is chemically bound to the cross-linked polymeric material;
    said sorbent being contained within a purification device within said compliant container, said sorbent being separated from said blood, blood product or physiologic fluid by a membrane wherein said membrane allows liquid comprising said undesirable molecules to pass through the membrane and contact said sorbent but where said membrane substantially excludes white blood cells, red blood cells and platelets from passing through said membrane and contacting said sorbent;
    wherein said hemocompatible material is supplied as slurry, or suspension, or dry powder or other dry particulate and said hemocompatible material is non-immobilized within the purification device; and
    wherein said storage container is a bag.

2. The storage container of claim 1, wherein said undesirable molecules are related to non-hemolytic transfusion reactions.

3. The storage container of claim 1, wherein said hemocompatible material comprises particles having a diameter in the range for 0.1 micron meters to 2 centimeters.

4. The storage container of claim 1, wherein said hemocompatible material is porous and has a pore structure that the total pore volume of pore size in the range of 50 Å to 10,000 Å is greater than 0.5 cc/g to 3.0 cc/g dry polymer.

5. The storage container of claim 1, wherein: said hemocompatible material is characterized as having a pore structure having a total volume of pore sizes in the range of from 10 Å to 10,000 Å greater than 0.5 cc/g to 3.0 cc/g of dry polymer; wherein the ratio of pore volume between 10 Å to 3,000 Å in diameter to pore volume between 500 Å to 3,000 Å in diameter of the said hemocompatible polymer is smaller than 7:1 and wherein the ratio of pore volume between 10 Å to 3,000 Å in diameter to pore volume between 10 Å to 6,000 Å in diameter of said hemocompatible polymer is less than 2:1.

6. The storage container of claim 1, wherein: said hemocompatible material is characterized as having a pore structure having a total volume of pore sizes in the range of from 20 Å to 10,000 Å is greater than 0.5 cc/g to 3.0 cc/g dry polymer; wherein the ratio of pore volume between 20 Å to 3,000 Å in diameter to pore volume between 500 Å to 3,000 Å in diameter of the said hemocompatible polymer is smaller than 7:1 and wherein the ratio of pore volume between 20 Å to 3,000 Å in diameter to pore volume between 20 Å to 6,000 Å in diameter of said hemocompatible polymer is less than 2:1.

7. The blood purification device of claim 1, wherein: said hemocompatible material is characterized as having a pore structure having a total volume of pore sizes in the range of from 50 Å to 10,000 Å is greater than 0.5 cc/g to 3.0 cc/g dry polymer; wherein the ratio of pore volume between 50 Å to 3,000 Å in diameter to pore volume between 500 Å to 3,000 Å in diameter of the said hemocompatible polymer is smaller than 7:1 and wherein the ratio of pore volume between 50 Å to 3,000 Å in diameter to pore volume between 50 Å to 6,000 Å in diameter of said hemocompatible polymer is less than 2:1.

8. The blood purification device of claim 1, where the hemocompatible material can sorb molecules from about 100 Daltons to approximately 1,000 kDa.

9. The blood purification device of claim 1, wherein said hemocomaptible material is derived from a pyrolyzed composition.

10. The blood purification device of claim 1, wherein said cross-linked polymeric material is pyrolyzed.

11. The blood purification device of claim 1, wherein said sorbent is pyrolyzed.

12. The blood purification device of claim 1, wherein said bag comprises a polymeric material comprising one or more of the following types of polymers: a polyvinyl chloride (PVC), a polyolefin (PO), a poly(ethylene-co-vinyl acetate) (EVA), and a fluorinated polyethylene propylene (FEP).

13. The blood purification device of claim 12, wherein the polymeric material further comprises a biocompatible plasticizer.

14. The blood purification device of claim 1, wherein said solid form sorbent further comprises a dispersing agent.

15. A method of treating blood, blood product, or physiologic fluid within a storage container comprising a bag, prior to transfusion of the blood, blood product, or physiologic fluid into a patient, to provide at least one of (i) increasing shelf life of the blood, blood product or physiologic fluid, (ii) maintaining freshness of new blood, blood product or physiologic fluid, and (iii) removing undesirable molecules from the blood, blood product or physiologic fluid through use of a sorbent, said sorbent being contained within a compliant container suitable for the storage of blood, blood products or physiologic fluid and said sorbent being separated from said blood, blood product of physiologic fluid by a membrane wherein said membrane allows liquid comprising said undesirable molecules to pass through the membrane and contact said sorbent but where said membrane substantially excludes white blood cells, red blood cells and platelets from passing thought said membrane and contacting said sorbent, said sorbent supplied as slurry, or suspension, or dry powder or other dry particulate and said sorbent is non-immobilized within the purification device and said sorbent comprises cross-linked polymeric material derived from the reaction of cross-linker with one or more of the following polymerizable monomers: divinylbenzene, styrene, ethylstyrene, acrylonitrile, butyl methacrylate, octyl methacrylate, butyl acrylate, octyl acrylate, cetyl methacrylate, cetyl acrylate, ethyl methacrylate, ethyl acrylate, vinyltoluene, vinylnaphthalene, vinylbenzyl alcohol, vinylformamide, methyl methacrylate, and methyl acrylate; wherein said sorbent comprises a hemocompatible surface comprising hydroxyethyl cellulose, hydroxypopyl cellulose, poly(hydroxyethyl methacrylate), poly(hydroxyethyl acrylate), poly(hydroxypropyl methacrylate), poly(hydroxypropyl acrylate), poly(dimethylaminoethyl methacrylate), poly(dimethylaminoethyl acrylate), poly (diethylamimoethyl methacrylate), poly-(diethylaminoethyl acrylate), poly(vinyl alcohol), heparin, polyethylene glycol, poly(N-vinylpyrrolidinone), salts of poly(methacrylic acid), salts of poly (acrylic acid) or copoplymers of mixtures thereof, wherein said hemocompatible surface is chemically bound to the cross-linked polymeric material.

16. The methods of claim 15, wherein said undesirable molecules are biologically active molecules (BAMs), biological response modifiers (BRMs), products of hemolysis, products of membrane or cellular degradation, toxins, drugs, antibodies, prions and similar molecules found in stored blood and blood products.

17. The method of claim 16, wherein the biologically active molecules comprise inflammatory mediators and stimulators.

18. The method of claim 17, wherein said inflammatory mediators and stimulators comprise cytokines, nitric oxide, thromboxanes, leukotrienes, platelet, activating factor, prostaglandins, glycoproteins, kinins, kininogens, complement factors, cell-adhesion molecules, superantigens, monokines, chemokines, interferons, free radicals, proteases, arachidonic acid metabolites, prostacyclins, beta endorphins, myocardial depressant factors, anandimide, 2-arachadonylglycerol, tetrahydrobiopterin, serotonin, histamine, bradykinin, soluble CD40 ligand, bioactive lipids, oxidized lipids, hemoglobin, red cell particulates, membrane or cellular components, growth factors, glycoproteins, prions, toxins, endotoxins, drugs, vasoactive substances, foreign antigens, and antibodies.

19. The method of claim 15 where undesirable molecules are antibodies.

20. The method of claim 15, wherein said sorbent is a hemocompatible polymer.

21. The method of claim 20, wherein said biocompatible polymer comprises particles having a diameter in the range for 0.1 micron meters to 2 centimeters.

22. The method of claim 20, wherein said hemocompatible polymer is porous and has a pore structure that the total pore volume of pore size in the range of 50 Å to 10,000 Å is greater than 0.5 cc/g to 3.0 cc/g dry polymer.

23. The method of claim 20, wherein said hemocompatible polymer is characterized as having a pore structure having a total volume of pore sizes in the range of from 10 Å to 10,000 Å is greater than 0.5 cc/g to 3.0 cc/g dry polymer; wherein the ratio of pore volume between 10 Å to 3,000 Å in diameter to pore volume between 500 Å to 3,000 Å in diameter of the said hemocompatible polymer is smaller than 7:1 and wherein the ratio of pore volume between 10 Å to 3,000 Å in diameter to pore volume between 10 Å to 6,000 Å in diameter of said hemocompatible polymer is less than 2:1.

24. The method of claim 20 where said hemocompatible polymer can sorb molecules from about 100 Daltons to approximately 1,000 kDa.

25. The method of claim 20, wherein said hemocompatible polymer is modified with ligands that specifically or non-specifically bind reactive biomolecules.

26. The method of claim 15, wherein said polymer may be porous or non-porous.

27. A method of making a blood purification device comprising
placing sorbent comprising hemocompatible material in a compliant container suitable for the storage of blood or blood products, said container comprising a bag;
wherein said hemocompatible material suitable for treating stored blood and blood products prior to transfusion of the blood, blood product, or physiologic fluid into a patient, said sorbent performing at least one of (i) increasing shelf life of the blood, blood product or physiologic fluid, (ii) maintaining freshness of new blood, blood product or physiologic fluid, and (iii) removing undesirable molecules from the blood, blood product or physiologic fluid; and
said sorbent being separated from said blood, blood product or physiologic fluid by a membrane wherein said membrane allows liquid comprising said undesirable molecules to pass through the membrane and contact said sorbent but where said membrane substantially excludes white blood cells, red blood cells and platelets from passing through said membrane and contacting said sorbent within said compliant container; said sorbent comprising a slurry, or suspension, or dry powder or other dry particulate and said sorbent is non-immobilized within the purification device;
wherein said sorbent comprises cross-linked polymeric material derived from the reaction of a cross-linker with one or more of the following polymerizable monomers: divinylbenzene, styrene, ethylstyrene, acrylonitrile, butyl methacrylate, octyl methacrylate, butyl acrylate, octyl acrylate, cetyl methacrylate, cetyl acrylate, ethyl methacrylate, ethyl acrylate, vinyltoluene, vinylnaphthalene, vinylbenzyl alcohol, vinylformamide, methyl methacrylate, and methyl acrylate;
wherein said sorbent comprises a hemocompatible surface comprising hydroxyethyl cellulose, hydroxypopyl cellulose, poly(hydroxyethyl methacrylate), poly(hydroxyethyl acrylate), poly(hydroxypropyl methacrylate), poly(hydroxypropyl acrylate), poly(dimethylaminoethyl methacrylate), poly(dimethylaminoethyl acrylate), poly(diethylamimoethyl methacrylate), poly-(diethylaminoethyl acrylate), poly(vinyl alcohol), heparin, polyethylene glycol, poly(N-vinylpyrrolidinone), salts of poly(methacrylic acid), salts of poly (acrylic acid) or copoplymers of mixtures thereof, wherein said hemocompatible surface is chemically bound to the cross-linked polymeric material.

28. The storage container of claim 1, wherein said storage container is capable of lowering the amount of Human Cytokine IL-8 in stored blood to a level lower than the initial Cytokine IL-8 level in said stored blood for a period of at least 41 days of storage.

* * * * *